US006318179B1

United States Patent
Hamilton et al.

(10) Patent No.: US 6,318,179 B1
(45) Date of Patent: Nov. 20, 2001

(54) ULTRASOUND BASED QUANTITATIVE MOTION MEASUREMENT USING SPECKLE SIZE ESTIMATION

(75) Inventors: James D. Hamilton, Menomonee Falls; Larry Y. L. Mo, Waukesha, both of WI (US); Gregory R. Bashford, Lincoln Lancaster, NE (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/597,603

(22) Filed: Jun. 20, 2000

(51) Int. Cl.[7] .............................. G01N 29/10; A61B 8/00
(52) U.S. Cl. .............................. 73/606; 73/620; 73/628; 73/861.25; 600/454; 600/456
(58) Field of Search ............................. 73/606, 620, 627, 73/625, 626, 628, 861.25, 618, 861.06; 600/437, 443, 447, 454, 456

(56) References Cited

U.S. PATENT DOCUMENTS

| | | |
|---|---|---|
| 5,398,216 | 3/1995 | Hall et al. |
| 5,517,995 * | 5/1996 | Klepper et al. ............ 600/447 |
| 5,522,393 * | 6/1996 | Phillips et al. ............ 73/861.25 |
| 5,570,691 * | 11/1996 | Wright et al. ............ 73/626 |
| 5,690,111 * | 11/1997 | Tsujino ............ 600/456 |
| 5,899,863 * | 5/1999 | Hatfield et al. ............ 600/443 |
| 5,928,153 * | 7/1999 | Chiang et al. ............ 600/454 |
| 6,074,348 * | 6/2000 | Chiao et al. ............ 600/443 |
| 6,120,450 * | 9/2000 | Li ............ 600/447 |

OTHER PUBLICATIONS

Anderson, Multi–Dimensional Velocity Estimation with Ultrasound Using Spatial Quadrature, IEEE Transactions on Ultrasonics, Ferroelectrics, and Frequency Control, vol. 45, No. 3, May (1998), pp. 852–861.

Newhouse et al., Invariance of Doppler Bandwidth With Flow Axis Displacement, IEEE 1990 Ultrasonics Symposium, pp. 1533–1536.

Trahey et al., Angle Independent Ultrasonic Detection of Blood Flow, IEEE 1987 Transactions on Biomedical Engineering, vol. BME–34, No. 12, Dec. 1987, pp. 965–967.

* cited by examiner

*Primary Examiner*—Hezron Williams
*Assistant Examiner*—Jacques Saint-Surin
(74) *Attorney, Agent, or Firm*—McAndrews, Held & Malloy, Ltd.; Peter J. Vogel; Michael A. Dellapenna

(57) ABSTRACT

An ultrasound system determines the relative movement in a first direction (F1) of first matter, such as blood flow, and second matter, such as an artery wall, in a subject under study (S). A beam (B1) of ultrasound waves defining a plurality of beam positions (BP1 and BP2) and beam axes (A1 and A2) are moved in scan directions having components parallel to direction F1. First and second blocks of data representing the first and second matter, respectively, are generated. A processor (20) performs an estimation of speckle size on first data to obtain a first result, and performs analysis of the second block of data to obtain a second result. The two results are analyzed to obtain a measure of the relative movement of the first and second matter.

30 Claims, 4 Drawing Sheets

ULTRASOUND BASED QUANTITATIVE MOTION MEASUREMENT USING SPECKLE SIZE ESTIMATION

BACKGROUND OF THE INVENTION

This invention relates to ultrasound and more particularly relates to determining quantitative movement, such as flow velocity, by using ultrasound.

Currently, most quantitative flow measurement done in ultrasound occurs along the scan axis, i.e., in the direction normal to the transducer face. If a method were devised that measured flow parallel to the transducer face, then the two could be combined to resolve the two-dimensional velocity vector in the scan plane. This concept would differ compared to existing lateral flow (i.e., movement parallel to the transducer face) measurement methods.

One method described by Newhouse and Reid ('Invariance of Doppler bandwidth with flow axis displacement', IEEE Ultrasonics Symposium Proceedings, 1990, p1533), measures the variance of the Doppler signals returned from lateral flow. A technique developed by M Anderson ('Multi-dimensional velocity estimation with ultrasound using spatial quadrature', IEEE Transactions on Ultrasonics, Ferroelectrics, and Frequency Control, vol. 45, no. 3, pp. 852–861) implements modified transducer apertures, creating ultrasound beams which produce modulated signals when scatters move laterally across the beam. Both these methods use no information from multiple ultrasound beam positions or scanning, and therefore differ from the techniques described in this specification. Another lateral flow method which measures direction and magnitude of local blood speckle pattern displacement using consecutive B-mode (i.e., gray scale) images was described by Trahey, Allison and Von Ramm (IEEE Transactions on Biomedical Engineering, vol. BME-34, No. 12, pp. 965–967). This technique requires multiple images and measures speckle position changes, unlike the preferred embodiment described in this specification which needs no such temporal measurements and estimates speckle size.

BRIEF SUMMARY OF THE INVENTION

The preferred embodiment is useful in an ultrasound system for imaging a subject under study including first matter and second matter, with first matter moving with respect to the second matter in a first direction. In such an environment, the preferred embodiment enables determination of the quantitative movement of the first matter with respect to the second matter by transmitting into the subject a beam of ultrasound waves having a predetermined size and defining a plurality of beam positions and a beam axis moved in one or more scan directions having one or more scan direction components parallel to the first direction. First reflected ultrasound waves are received from the first matter and second ultrasound waves are received from the second matter in response to the beam positions in the one or more scan directions. The transmitting and receiving preferably are accomplished with a transducer assembly. A first block of data is generated in response to the first reflected ultrasound waves representing at least one component of movement of the first matter with respect to the second matter along one of the scan directions. A second block of data is generated in response to the reflected second ultrasound waves representing a portion of the second matter. A first analysis of the first block of data is performed to obtain a first result; a second analysis of the second block of data is performed to obtain a second result; and a third analysis of the first result and the second result is performed to determine one or more movement characteristics of the first matter. The generating of the blocks of data and the performing of the analyses preferably is accomplished with a processor. The one or more movement characteristics are displayed, preferably with a display unit.

By using the foregoing techniques, movement can be detected by ultrasound with a degree of accuracy and convenience previously unavailable.

DETAILED DESCRIPTION OF THE INVENTION

The preferred embodiment measures ultrasound speckle size and relates it to tissue motion. The speckle, produced by coherent sound waves undergoing multiple scattering within a resolution cell of the imaging system, changes size laterally depending on the tissue movement and the rate which the ultrasound beam is scanned through the subject.

Figure 1:
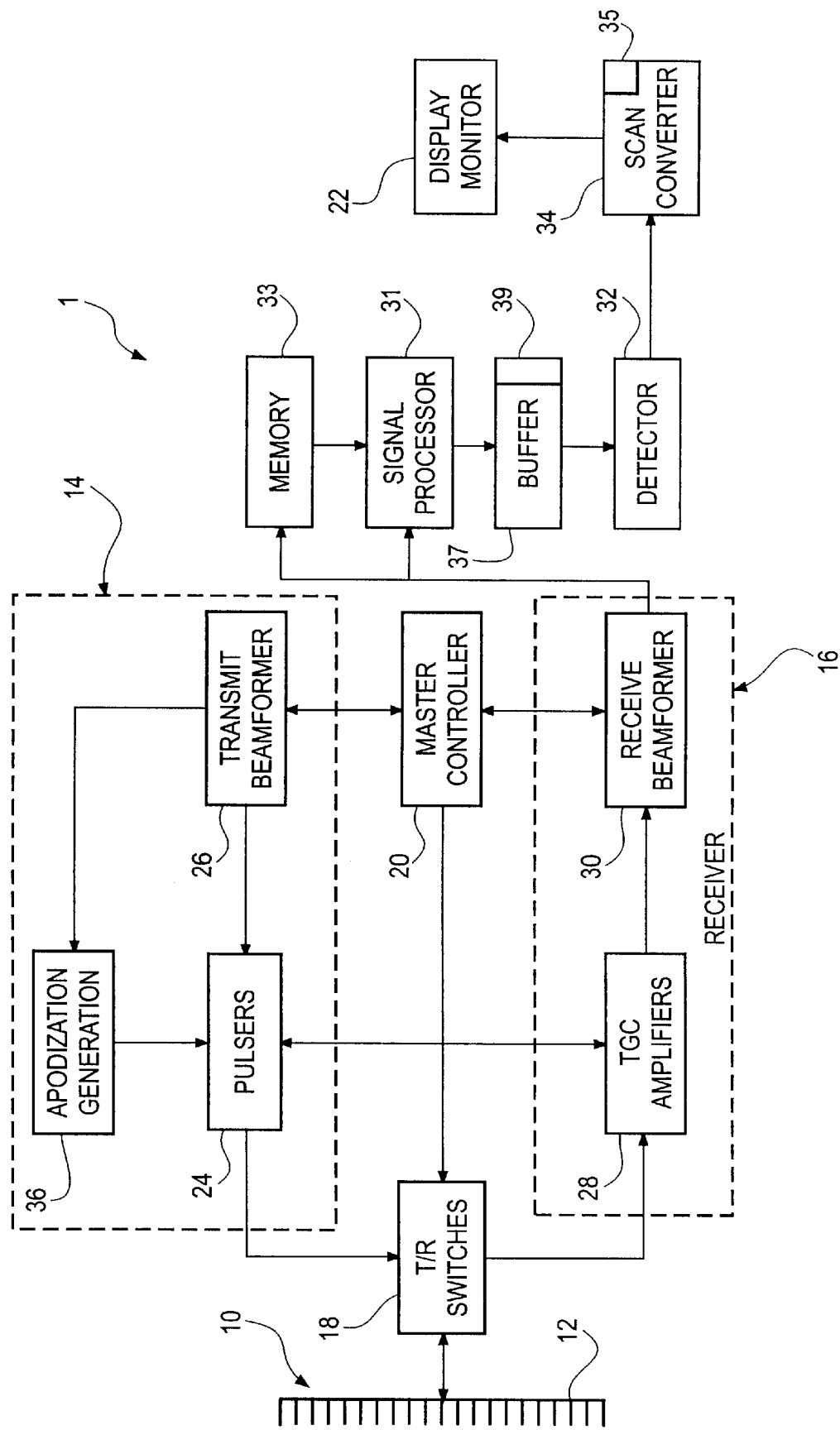
FIG. 1 is a schematic block diagram of a preferred embodiment of the present invention.

Referring to FIG. 1, a preferred form of ultrasound system 1 made in accordance with the invention comprises a transducer array 10 including a plurality of separately driven transducer elements 12, each of which produces a burst of ultrasonic energy when energized by a pulsed or coded waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller or processor 20 responsive to commands by a human operator. Processor 20 may comprise a variety of processors, such as a microprocessor, digital signal processor, or an ASIC capable of logical and arithmetic operations. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal which is used to produce a line in an image on a display monitor 22.

Under the direction of master controller 20, transmitter 14 drives transducer array 10 such that the ultrasonic energy is transmitted as a directed focused beam. To accomplish this, respective time delays are imparted to a plurality of pulsers 24 by a transmit beamformer 26. Master controller 20 determines the conditions under which the acoustic pulses will be transmitted. With this information, transmit beamformer 26 determines the timing and amplitudes of each of the transmit pulse or coded waveform to be generated by pulsers 24. The amplitudes of each transmit signal are generated by an apodization generation circuit 36, which may be a high-voltage controller that sets the power supply voltage to each pulser. Pulsers 24 in turn send the transmit pulses to each of elements 12 of transducer array 10 via T/R switches 18, which protect time-gain control (TGC) amplifiers 28 from the high voltages which may exist at the transducer array. Weightings are generated within apodization generation circuit 36, which may comprise a set of digital-to analog converters that take the weighting data from transmit beamformer 26 and apply it to pulsers 24. By appropriately adjusting the transmit focus time delays in a conventional manner and also adjusting the transmit apodization weightings, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the magnitude of the echo signal at a particular point in time represents the amount of reflection occurring at a specific range. Due to differences in the propagation paths between a reflecting point and each transducer element 12, the echo signals will not be detected simultaneously and their amplitudes will not be equal. Receiver 16 amplifies the separate echo signals via a respective TGC amplifier 28 in each receive channel. The amount of amplification provided by the TGC amplifiers is controlled through a control path (not shown) that is driven by a TGC circuit (not shown), the latter being set by the master controller and hand operation of potentiometers. The amplified echo signals are then fed to a receive beamformer 30. Each receiver channel of the receive beamformer is coupled to a respective one of transducer elements 12 by a respective TGC amplifier 28.

Under the direction of master controller 20, receive beamformer 30 tracks the direction of the transmitted beam. Receive beamformer 30 imparts the proper time delays and receive apodization weightings to each amplified echo signal and sums them to provide an echo signal which accurately indicates the total ultrasonic energy reflected from a point located at a particular range along one ultrasonic beam. The receive focus time delays are computed in real-time using specialized hardware or are read from a look-up table. The receive channels also have circuitry for filtering the received pulses. The time-delayed receive signals are then summed and supplied to a signal processor 31 and memory 33. The signal processor 31 may be controlled by the master controller 20 and filters summed echo signals removing noise and undesired signal components. In addition, decoding of coded waveforms maybe performed by the signal processor 31. For both functions, stored echo signals from memory 33 may be used. The processed signals are supplied to memory buffer 37 which stores echo lines corresponding to segments of or entire image frames. Detector 32 converts the receive signals to display data. In the B-mode (gray scale), this is the envelope of the signal with some additional processing, such as edge enhancement and logarithmic compression. A scan converter 34 receives the display data from detector 32 and converts the data into the desired image for display. In particular, scan converter 34 converts the acoustic image data from polar coordinate (R—θ) sector format or Cartesian coordinate linear array to appropriately scaled Cartesian coordinate display pixel data at the video rate. These scan-converted acoustic data are then provided for display on display monitor 22, which images the time-varying amplitude of the signal envelope as a gray scale. A respective scan line is displayed for each transmit beam.

In general, the preferred embodiment measures the lateral size of speckle corresponding to relative movement of matter in a subject under study, such as blood flow or tissue motion. Depending on the scan sequence direction, speckle corresponding to moving targets or matter will either expand or contract in the direction of motion. Comparing the expanded/compressed size relative to speckle corresponding to stationary targets allows quantitative lateral flow measurement through a transfer function which can be experimentally obtained by those skilled in the art of ultrasound.

According to an algorithm made in accordance with the preferred embodiment, the speckle corresponding to flow is first enhanced by using the "Bflow" techniques described above and described in more detail in U.S. application Ser. No. 09/065,212, filed Apr. 23, 1998 in the names of Richard Chiao et al., (hereafter the "'212 Application," a Continuation-In-Part of application Ser. No. 09/052,789, filed Mar. 31, 1998, now abandoned) which is assigned to the parent of the assignee of the present application and which is incorporated by reference in its entirety into this application. The FIG. 1 apparatus may be modified as taught in the '212 Application and the B-flow techniques taught in the '212 Application may be used to further enhance the speckle data obtained by using the modified apparatus; alternatively, a similar method of enhancing the speckle data may be used.

Figure 2:
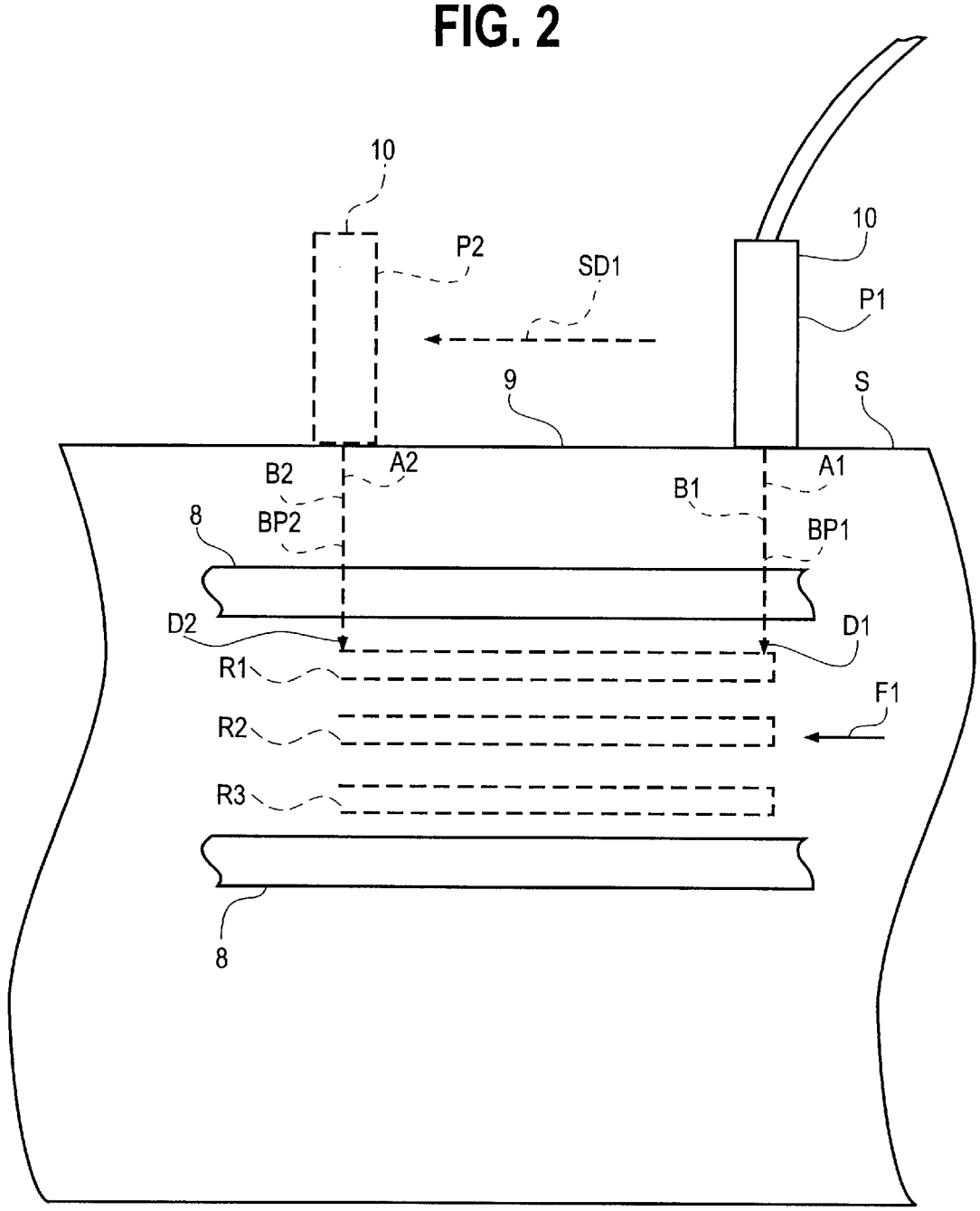
FIG. 2 is a schematic block diagram of the ultrasound transducer shown in FIG. 1 illustrating a preferred form of manual manipulation of the transducer in accordance with a preferred embodiment of the invention in order to define rows of data in a region of interest.

FIG. 2 illustrates manual manipulation of transducer assembly 10 in order to direct beams of ultrasound waves into a subject S having a surface 9. The transducer may start in a position P1 resting on surface 9 and may generate a beam of ultrasound waves B1 which defines a beam axis A1 and a beam position BP1. Beam B1 can be varied in size, shape and frequency by master controller 20 and pulsers 24 in accordance with well known techniques. Beam B1 is directed along axis A1 in direction D1.

Still referring to FIG. 2, transducer 10 is manually moved in a scan direction SD1 along surface 9 so that beams are transmitted into subject S along a plurality of positions between position P1 and another position P2 which defined beam positions BP1 and BP2, respectively. Beams transmitted at these intermediate positions may vary in size, shape, frequency and direction as set by master controller 20 and pulsers 24 in accordance with well known techniques. At position P2, transducer generates a beam B2 which defines a beam axis A2 at beam position BP2. Beam B2 can be varied in size, shape and frequency by master controller 20 and pulsers 24. Beam B2 is directed along axis A2 in direction D2. Beams B1 and B2 (as well as beams generated intermediate between positions P1 and P2) are transmitted to several regions within subject S, such as regions R1–R3 which may correspond to material, such as blood, moving or flowing in a flow direction F1. Regions R1–R3 also may correspond to rows of moving matter within subject S. The flow may be confined to the walls of an artery, such as wall 8, shown in cross section in FIG. 1. Scan direction SD1 has a component parallel to direction F1.

Figure 3:
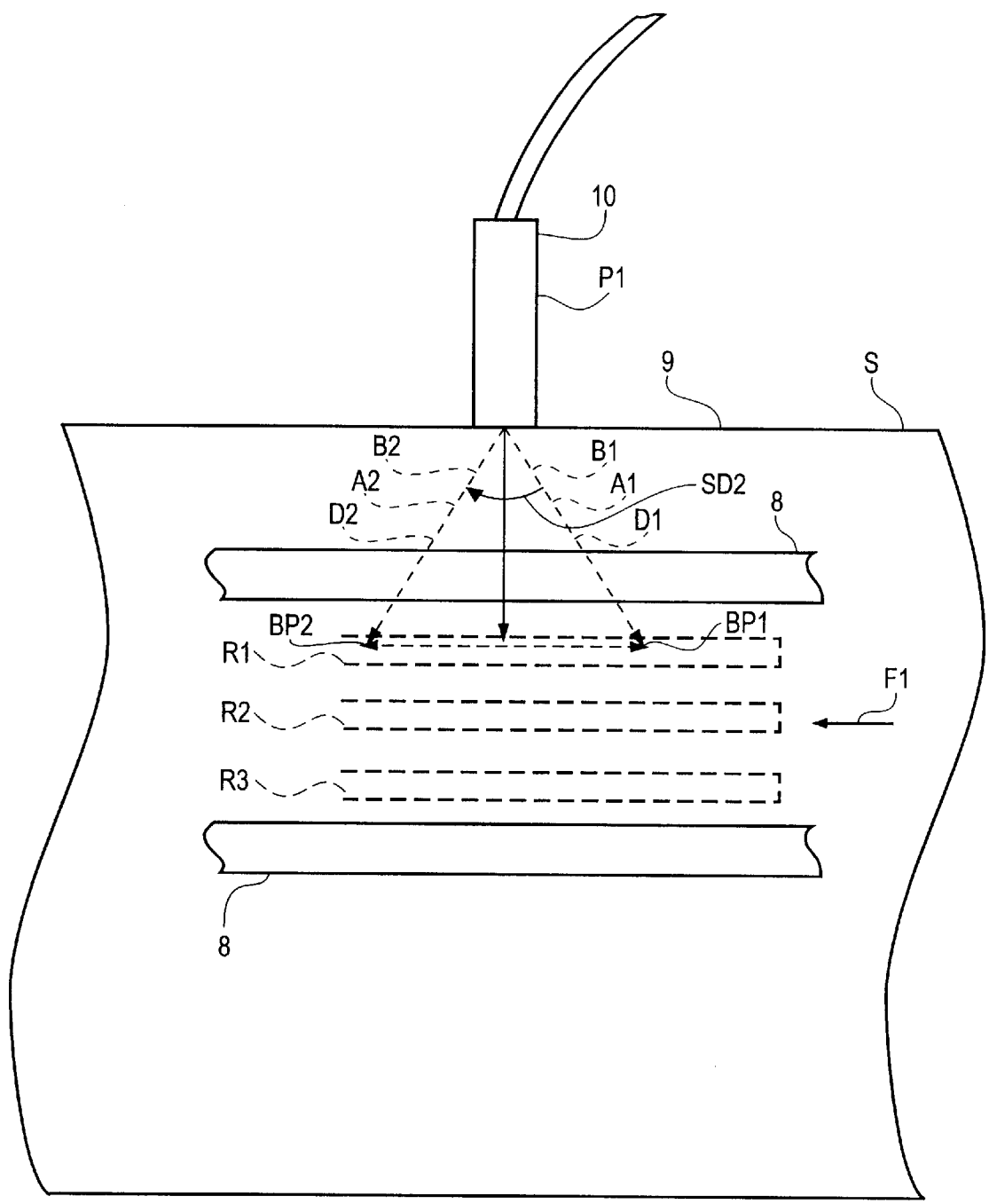
FIG. 3 is a schematic block diagram of the transducer show in FIG. 2 illustrating a preferred form of electronic beam forming in accordance with a preferred embodiment of the invention in order to define rows of data in a region of interest

FIG. 3 illustrates the generation of beams B1 and B2 by electronic beamforming in connection with transducer 10. The beamforming may be conducted, for example, in the manner described in U.S. Pat. No. 5,398,216 issued Mar. 14, 1995 in the name of Anne L. Hall et al., assigned to a parent of the assignee of the present application, and incorporated by reference into this application. According to the FIG. 3 embodiment, transducer 10 remains in position P1, and beams, with end points B1 and B2 which extend in directions D1 and D2, are moved through a scan direction SD2 which forms a circular arc as shown, with end beam positions BP1 and BP2, as well as intermediate beam positions. Scan direction SD2 has components parallel to direction F1.

Transducer 10 receives first ultrasound waves reflected from regions R1–R3 and generates corresponding first transducer signals in a well known manner. Transducer 10 also receives second ultrasound waves reflected from wall 8 and generates corresponding second transducer signals. The first and second transducer signals are used to generate corresponding first and second Bflow data enhanced in the manner described in the '212 Application. The enhanced data is stored in a memory 35 which may be part of scan converter 34. The data is displayed in a B-mode type display on display monitor 22.

Using the image on display monitor 22, a user of transducer 10 selects a region-of-interest (ROI) corresponding to moving matter, tissue or blood. The region of interest may include regions R1–R3. The data corresponding to the ROI may be transferred to and stored in memory 35 as an intensity image or in memory 39 as pre-detection echo data. To illustrate the motion estimation procedure, intensity image data will be considered here, however similar processing maybe used to analyze pre-detection echo signals. Each row in this image (e.g., rows R1–R3) is represented by packets of data corresponding to a one-dimensional lateral speckle signal. For each row, the full-width-half-maximum (FWHM) of the autocovariance function (ACVF) of the data corresponding to the row, or segments of the row, is measured from the corresponding packet of data. The FWHM-ACVF's for the image rows or image row segments may be combined in various ways depending on the application, e.g. averaging, to obtain a one or two dimensional map of FWHM-ACVF's representing speckle size within the ROI.

Each value of the FWHM-ACVF is the input to a transfer function, of which the output is the estimated velocity. The transfer function may be a simple linear relationship with velocity, or it may be a more complex nonlinear function. Another parameter to the transfer function may be the FWHM-ACVF of speckle corresponding to stationary targets, such as the data resulting from wall 8.

In addition, the scan sequence direction (e.g., SD1 or SD2) relative to the flow direction (e.g., F1) determines whether the speckle is expanded or compressed. If the scan sequence direction is the same as the lateral flow direction, the speckle will expand or "smear" more as velocity approaches the scan rate, defined as the speed the beam is swept through the subject. For this reason, scan rate shall be controlled based on the desired velocity range to be measured. For example, referring to FIG. 2, the average scan rate would be the difference between beam positions BP1 and BP2 divided by the time to acquire all beams. Speckle expansion does not occur if the scan direction is opposite the flow, therefore, to ensure suitable data is acquired (i.e., expanded speckle providing velocity estimation), the FWHM-ACVF might be measured in the ROI twice; once for each scan sequence direction. The three parameters (all FWHM-ACVF; one with scan sequence direction with flow, one with scan sequence direction against flow, and one with stationary speckle) may be fed into a nonlinear transfer function, or a look-up table, to determine the velocity magnitude and direction.

Figure 4:
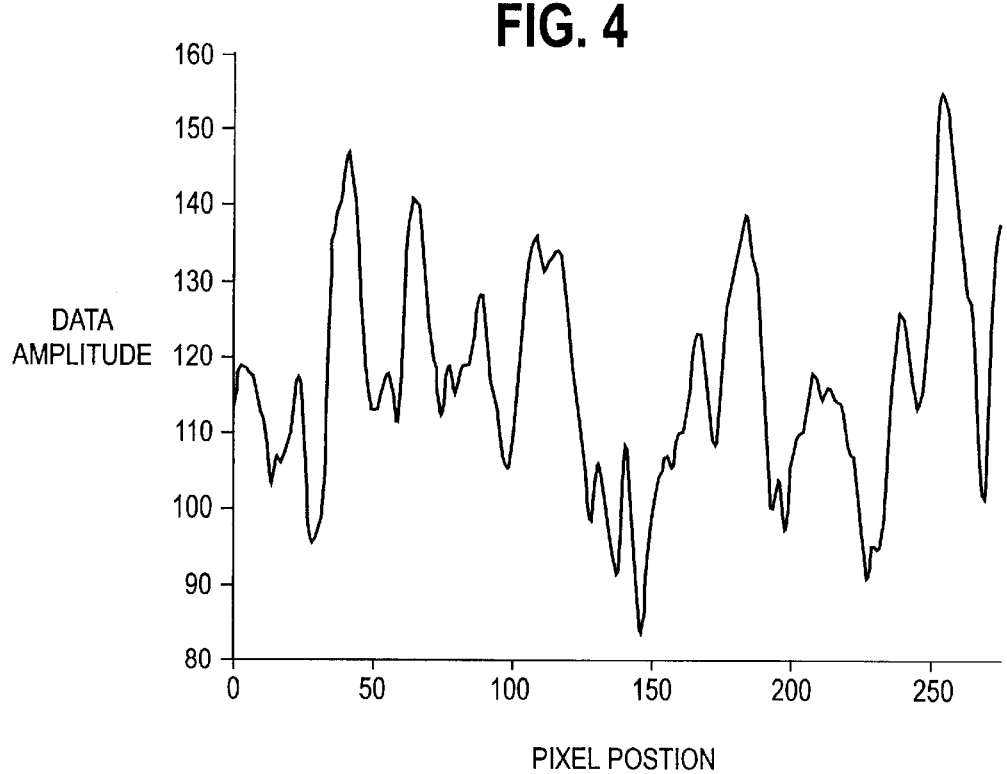
FIG. 4 is a graph illustrating intensity vs. pixel position for one of the rows illustrated in FIG. 2 or FIG. 3.

FIG. 4 illustrates a graph of an exemplary data obtained from row R1 in FIG. 2 or FIG. 3. The vertical or Y axis represents intensity of the speckle signal and the horizontal or x axis represents the position of the intensity along row R1 as shown in FIG. 2 or FIG. 3. The autocovariance function of x(t) can be estimated as:

$$R(\tau) = \int \tilde{x}(t)\tilde{x}(t+\tau)dt$$

where $\tilde{x}(t)$ is x(t) with its mean removed. Furthermore, if x(t) is complex (i.e., real and imaginary parts) as the case may be with echo data before detection, the auto covariance can be written:

$$R(\tau) = \int \tilde{x}(t)\tilde{x}^*(t+\tau)dt$$

where * denotes complex conjugation. Using the above lateral speckle signal shown in FIG. 4 as x(t), the central portion of the autocovariance function may be plotted as shown in FIG. 5.

Figure 5:
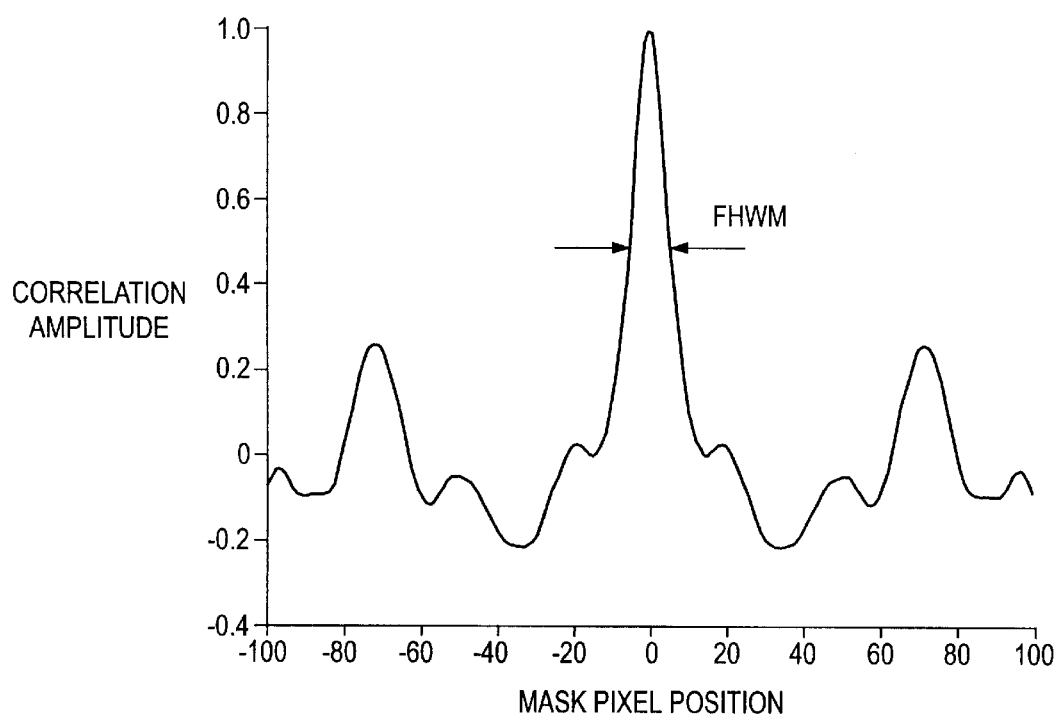
FIG. 5 is a graph illustrating intensity power vs. mask pixel position for the data illustrated in FIG. 4.

The function may be analogized to a process of arranging two masks, each corresponding to the data plotted in FIG. 4, sliding the masks relative to each other in a horizontal direction according to the pixel positions represented on the x axis in FIG. 5, multiplying the resulting values, and plotting the product. Of course, the product would not actually need to be plotted in order to represent the correlation function for purposes of the preferred embodiment. However, the function is plottable in the manner shown in FIG. 5. Those skilled in the art recognize how useful results can be obtained from a correlation function without actually plotting the function.

The parameter of interest in connection with FIG. 5 is the FWHM of this correlation function. In practice, widths at other fractions of the maximum or other characteristics of the correlation function (e.g., derivative, variance, integral) may also be used. For the FIG. 5 graph, the FWHM is 10.4 units, which corresponds to a spatial metric (e.g., speckle size). This is the first result obtained by the algorithm. A second result is obtained when the FWHM-ACVF of speckle signal corresponding to stationary targets in the same image (e.g., wall 8) is calculated in the same manner, giving a parameter of 5.0 units. This second result shows that the speckle has "stretched" in the direction of the flow F1.

The transfer function producing the relative velocity estimates from the above described correlation processing of ultrasound speckle data will depend on the ultrasound beam characteristics such as size, shape and frequency. These determine the character of stationary speckle. In addition, the beam scan rate sets the speckle stretching behavior of moving tissue or blood. To ascertain the actual transfer function requires experimentation and modeling of these factors. Those skilled in the art know how to obtain an actual transfer function by conducting well known experiments depending on the imaging characteristics of the ultrasound system. For example, the results of the data plotted in FIG. 5 would be compared with the results of an analysis of the data obtained from stationary matter, such as wall 8, and the two results would be compared to a known value of velocity measured from an independent source. A look up table could be prepared from the results of measurements at various known velocities in order the obtain a transfer function.

Those skilled in the art recognize that the preferred embodiments may be altered and modified without departing from the true spirit and scope of the invention as defined in the accompanying claims.

What is claimed is:

1. In an ultrasound system for imaging a subject under study including first matter moving in a first direction relative to second matter, apparatus for determining the quantitative movement of the first matter with respect to the second matter comprising:

a transducer assembly operable to transmit into the subject a beam of ultrasound waves having a predetermined size and shape and defining a plurality of beam positions and a beam axis moved at a predetermined rate in one or more scan directions having one or more scan direction components parallel to said first direction, said transducer assembly receiving first reflected ultrasound waves from said first matter and second reflected ultrasound waves from said second matter in response to said beam positions in said one or more scan directions;

a processor responsive to the first reflected ultrasound waves to generate a first block of data representing at least one component of movement of said first matter with respect to said second matter along one of said scan directions, responsive to said reflected second ultrasound waves to generate a second block of data representing a characteristic of a portion of said second matter, to perform a first analysis of said first block of data to obtain a first result, to perform a second analysis of said second block of data to obtain a second result, to perform a third analysis of said first result and said second result to determine one or more movement characteristics of said first matter; and a display for displaying said one or more movement characteristics of said first matter.

2. Apparatus, as claimed in claim 1, wherein said transducer assembly is movable manually in order to move said beam in said one or more scan directions.

3. Apparatus, as claimed in claim 1, wherein said transducer assembly is an array of transducer elements capable of transmitting and receiving ultrasound waves using electronic beamforming to produce time delayed ultrasound pulses to move said beam in said one or more scan directions.

4. Apparatus, as claimed in claim 1, wherein said first block of data represents a signal intensity map of the first reflected ultrasound waves.

5. Apparatus, as claimed in claim 1, wherein said first matter comprises regions at a plurality of locations within said subject and wherein said first block of data comprises separate packets of data representing said regions.

6. Apparatus, as claimed in claim 5, wherein said analysis of said first block of data comprises separate analysis on each of said packets of data.

7. Apparatus, as claimed in claim 1, wherein said first analysis comprises correlation analysis of signals representing reflected ultrasound waves having a result plottable as a graph.

8. Apparatus, as claimed in 7, wherein said correlation analysis is performed along said scan direction.

9. Apparatus, as claimed in 1, wherein correlation analysis is a calculation of the autocorrelation function of signals representing reflected ultrasound waves.

10. Apparatus, as claimed in claim 9, wherein said first analysis further comprises analysis performable on the width of a predetermined portion of said result plottable as a graph.

11. Apparatus, as claimed in claim 10, wherein said predetermined portion comprises the half maximum value of said graph.

12. Apparatus, as claimed in claim 11, wherein said second analysis comprises correlation analysis having a result plottable as a second graph and further comprises an analysis of the width of the half maximum value of said second graph.

13. Apparatus, as claimed in claim 1, wherein said one or more scan direction components comprise components extending in said first direction and components extending opposite said first direction.

14. Apparatus, as claimed in claim 1, wherein said third analysis comprises executing a transfer function to determine velocity of at least a portion of said first matter with respect to said second matter.

15. Apparatus, as claimed in claim 14, wherein said one component of movement represents regions of said first matter at a plurality of locations within said subject and wherein said first block of data comprises separate packets of data representing said regions and wherein said transfer function separately determines the velocities of the first matter in said regions.

16. In an ultrasound system for imaging a subject under study including first matter moving in a first direction with respect to the second matter, a method of determining the quantitative movement of the first matter with respect to the second matter comprising:

transmitting into the subject a beam of ultrasound waves having a predetermined size and defining a plurality of beam positions and a beam axis moved in one or more scan directions having one or more scan direction components parallel to said first direction;

receiving first reflected ultrasound waves from said first matter and second reflected ultrasound waves from said second matter in response to said beam positions in said one or more scan directions;

generating a first block of data representing at least one component of movement of said first matter with respect to said second matter along one of said scan directions in response to said first reflected ultrasound waves;

generating a second block of data representing a characteristic of a portion of said second matter in response to said second reflected ultrasound waves;

performing a first analysis of said first block of data to obtain a first result;

performing a second analysis of said second block of data to obtain a second result;

performing a third analysis of said first result and said second result to determine one or more movement characteristics of said first matter; and displaying said one or more movement characteristics of said first matter.

17. A method, as claimed in claim 16, wherein said transmitting comprises manual movement in order to move said beam in said plurality of positions and one or more scan directions.

18. A method, as claimed in claim 16, wherein said transmitting comprises electronic beamforming to produce time delayed ultrasound pulses to move said beam in said one or more scan directions.

19. A method, as claimed in claim 16, wherein said first block of data represents a signal intensity map of the first reflected ultrasound waves.

20. A method, as claimed in claim 16, wherein said first matter comprises regions at a plurality of locations within said subject and wherein said first block of data comprises separate packets of data representing said regions.

21. A method, as claimed in claim 20, wherein said analysis of said first block of data comprises separate analysis on each of said packets of data.

22. A method, as claimed in claim 16, wherein said first analysis comprises correlation analysis of signals representing reflected ultrasound waves having a result plottable as a graph.

23. A method, as claimed in 22, wherein said correlation analysis is performed along said scan direction.

24. A method, as claimed in 16, wherein correlation analysis is a calculation of the autocorrelation function of signals representing reflected ultrasound waves.

25. A method, as claimed in claim 24, wherein said first analysis further comprises analysis performable on the width of a predetermined portion of said result plottable as a graph.

26. A method, as claimed in claim 25, wherein said predetermined portion comprises the half maximum value of said graph.

27. A method, as claimed in claim 26, wherein said second analysis comprises correlation analysis having a result plottable as a second graph and further comprises an analysis of the width of the half maximum value of said second graph.

28. A method, as claimed in claim 16, wherein said one or more scan direction components comprise components extending in said first direction and components extending opposite said first direction.

29. A method, as claimed in claim 16, wherein said third analysis comprises executing a transfer function to determine velocity of at least a portion of said first matter with respect to said second matter.

30. A method, as claimed in claim 29, wherein said one component of movement represents regions of said first matter at a plurality of locations within said subject and wherein said first block of data comprises separate packets of data representing said regions and wherein said transfer function separately determines the velocities of the first matter in said regions.

* * * * *